US006486152B1

United States Patent
Coles et al.

(10) Patent No.: US 6,486,152 B1
(45) Date of Patent: Nov. 26, 2002

(54) TOPICAL CARBAMAZEPINE FORMULATIONS AND METHODS OF USE

(75) Inventors: Marc Coles, Neot Nordia; Gad Keren, Kiriat Ono, both of (IL)

(73) Assignee: Taro Pharmaceutical Industries Ltd. (IL)

( * ) Notice: Subject to any disclaimer, the term of this patent is extended or adjusted under 35 U.S.C. 154(b) by 0 days.

(21) Appl. No.: 09/597,561

(22) Filed: Jun. 19, 2000

Related U.S. Application Data

(62) Division of application No. PCT/US98/26919, filed on Dec. 18, 1998.
(60) Provisional application No. 60/068,370, filed on Dec. 19, 1997.

(51) Int. Cl.[7] .............................................. A61K 31/55
(52) U.S. Cl. ....................................... 514/217; 514/863
(58) Field of Search ................... 514/217, 863

(56) References Cited

U.S. PATENT DOCUMENTS

| | | | |
|---|---|---|---|
| 4,034,087 A | | 7/1977 | Voorhees |
| 4,758,554 A | * | 7/1988 | Sorenson |
| 5,122,543 A | | 6/1992 | Khanna |
| 5,234,929 A | | 8/1993 | Chelen |
| 5,466,683 A | * | 11/1995 | Sterling et al. |
| 5,472,954 A | | 12/1995 | Loftsson |
| 5,662,926 A | | 9/1997 | Wick et al. |
| 5,900,249 A | * | 5/1999 | Smith |

FOREIGN PATENT DOCUMENTS

| | | |
|---|---|---|
| DE | 43 44 661 | 6/1995 |
| EP | 0 435 526 A | 7/1991 |
| WO | WO 95 25504 A | 9/1995 |
| WO | WO 96 1430 A | 5/1996 |

OTHER PUBLICATIONS

Harel, A., et al., Effect of Carbamazepine on HaCaT Keratinocyte Proliferation and Inflammatory State (A Possible Role for Carbamazepine in Psoriasis), presented at an international conference during Sep.–Nov., 1997.

Smith, K.T., and Skelton, H.G., Accidental Success with Carbamazepine for Psoriatic Erythroderma, New England Journal of Medicine, Dec. 26, 1996, pp. 1999–2000.

Smith, K.J., et al. "Therapeutic efficacy of carbamazepine in a HIV–1–positive patient with psoriatic erythroderma," J. Am. Acad. Dermatol. 1997;37:851–4. Nov.

"Carbamazepine," the Merck Index (12th Edition), p. 290, 1996.

"Carbamazepine," the Merck Index (12th Edition), p. 290, 1996.

* cited by examiner

*Primary Examiner*—William R. A. Jarvis
*Assistant Examiner*—Vickie Kim
(74) *Attorney, Agent, or Firm*—Venable; Michael A. Gollin

(57) ABSTRACT

A therapeutic formulation comprises a topically acceptable semisolid vehicle and carbamazepine, the vehicle consisting of components that are compatible with the carbamazepine, and the carbamazepine being in a concentration sufficient to permit a therapeutically effective amount of the carbamazepine to be absorbed from the formulation into the skin of a patient. The vehicle may be a cream, ointment, or gel. A method of treating a skin condition of a patient such as psoriasis comprises applying carbamazepine topically to the patient's skin until the condition improves. A method of administering carbamazepine to a patient comprises applying a formulation comprising carbamazepine topically to the patient's skin.

27 Claims, No Drawings

TOPICAL CARBAMAZEPINE FORMULATIONS AND METHODS OF USE

This application claims benefit of PCT/US98/26919 filed Dec. 18, 1998 which claims benefit of 60/068,370 filed Dec. 19, 1997.

BACKGROUND OF THE INVENTION

The invention relates to topical formulations of carbamazepine and their use in treating skin conditions such as psoriasis.

Carbamazepine and derivatives are well-known as systemic bioactive agents useful as anticonvulsants. They are used in treating central nervous system such as epilepsy. A review of patents referring to carbamazepine reveals that there has been ongoing research into oral formulations of carbamazepine, intravenous formulations, sustained release delivery systems including a transdermal patch, and uses for treating other central nervous system disorders, motion sickness, parkinsonian syndromes, drug dependency such as alcoholism, and cocaine use. These formulations are all directed to systemic applications, and the therapeutic targets are all essentially neurological diseases and conditions.

Systemic use of drugs has disadvantages, such as the need for high dosages, side effects at regions of the body unrelated to the affected tissue, toxicity to the liver or other organs, and slow or overly long-lasting results. Carbamazepine may cause neuropathy, adverse hematologic effects such as anemia, and a hypersensitivity syndrome including dermatitis. The side effects can be severe requiring discontinuation of therapy in some patients. Nonetheless, carbamazepine has been believed to be a drug that is only effective in systemic applications. Its mechanisms of action and metabolism are poorly understood. It would be desirable to find new ways of delivering carbamazepine with reduced side effects.

Psoriasis is a disease of poorly understood etiology. There has been a limited arsenal of therapeutic methods useful in treating the disease, including physical treatment (sun, local heating, mud treatment), and steroids. The beneficial effects of these approaches are limited. None is effective in all cases, and the failure rate is high. Any effective new method of treatment would be of enormous value in relieving the pain of people with psoriasis.

SUMMARY OF THE INVENTION

According to the invention, topical formulations of carbamazepine comprise a pharmaceutically acceptable vehicle in which a suitable concentration of carbamazepine is dissolved or suspended, the drug and vehicle interacting such that a topically effective amount of the carbamazepine may be transferred to epidermal tissue to which the formulation is applied. The invention also encompasses a method of treating psoriasis comprising applying an effective amount of a topical formulation of carbamazepine to the affected area until the condition is improved. This provides a new treatment modality using a new active agent.

A therapeutic formulation comprises a topically acceptable semisolid vehicle and carbamazepine, the vehicle consisting of components that are compatible with the carbamazepine, and the carbamazepine being in a concentration sufficient to permit a therapeutically effective amount of the carbamazepine to be absorbed from the formulation into the skin of a patient. The vehicle may be a cream, ointment, or gel. A method of treating a skin condition of a patient such as psoriasis comprises applying carbamazepine topically to the patient's skin until the condition improves. A method of administering carbamazepine to a patient comprises applying a formulation comprising carbamazepine locally to an affected area, preferably topically to the patient's skin.

Further objectives and advantages will become apparent from a consideration of the description and drawings.

DETAILED DESCRIPTION OF THE PREFERRED EMBODIMENTS

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

It was observed that an HIV positive patient suffering from psoriatic erythroderma exhibited improvement when he accidentally ingested 200–400 mg/day of Tegretol® carbamazepine for two weeks. The condition flared up again after he stopped taking the medication. The condition improved once again when he intentionally began taking the medication for a second time. His mood was affected, too. Smith and Skelton, New England Journal of Medicine, Dec. 26, 1996, page 1999.

According to the invention, similar effectiveness may be achieved in a topical formulation whose use minimizes the psychological and other side effects of carbamazepine administered systemically. Such a formulation is a semisolid or non solid suitable for spreading on the affected tissue of a patient. The formulation may be a cream, ointment, gel, lotion, or liquid, and may be occlusive and moisturizing. An oil-in-water emulsion providing an elegant cream base is most preferred. A liquid is desirable for treating the scalp.

The components of the formulation are selected to be compatible, stable, topically acceptable, and able to support carbamazepine in a chemically stable state, and to deliver it into the skin of a patient upon application. The carbamazepine may be present as a suspension or a solution. A solution is preferred in order to facilitate prompt drug delivery. Carbamazepine is practically insoluble in water but is soluble in alcohols, acetone, and propylene glycol. Accordingly, propylene glycol containing vehicles are preferred.

The carbamazepine may be made into pharmaceutical compositions with appropriate pharmaceutically acceptable carriers or diluents and may be formulated into semi-solid or liquid forms. Methods known in the art can be utilized to control release or absorption of the composition over time. A pharmaceutically-acceptable form should be employed which does not in effectuate the compositions of the present invention.

The compositions may be used alone or in appropriate association, as well as in combination with, other pharmaceutically-active compounds. The formulation may further comprise antiinflammatory components such as steroids or non-steroid compounds, and may comprise local anesthetics. The method and composition of the invention may be used in combination or in rotation with other treatment regimes, to avoid the desensitization effect occurring with psoriasis and other skin diseases.

"Non-solid" is meant to exclude solid dosage forms such as tablets, and includes gels, creams, ointments, lotions, liquids, and suspensions.

The term "treatment" is intended to encompass administration of compounds according to the invention prophylactically to prevent or suppress an undesired condition, and therapeutic administration to eliminate or reduce the extent or symptoms of the condition. Treatment according to the invention may be for a human or an animal having a disease in need of such treatment.

The "effective amount" of the composition is such as to produce the desired effect in a host which can be monitored using several end-points known to those skilled in the art. For example, one desired effect might comprise reduction of psoriatic inflammation. Such effects could be monitored in terms of a therapeutic effect, e.g., alleviation of some symptom associated with the disease being treated, or particularized assays. These methods described are by no means all-inclusive, and further methods to suit the specific application will be apparent to the ordinary skilled artisan.

Furthermore, the amounts of each active agent included in the compositions employed in the examples described herein provide general guidance of the range of each component to be utilized by the practitioner upon optimizing the method of the present invention for practice either in vitro or in vivo. Moreover, such ranges by no means preclude use of a higher or lower amount of a component, as might be warranted in a particular application. For example, the actual dose and schedule may vary depending on whether the compositions are administered in combination with other pharmaceutical compositions, or depending on interindividual differences in severity, pharmacokinetics, drug disposition, and metabolism. One skilled in the art can easily make any necessary adjustments in accordance with the necessities of the particular situation.

The concentration of carbamazepine in such a formulation is high enough to permit delivery of a therapeutically effective amount, but not so high as to cause unwanted side effects. A preferred concentration is between about 0.05% and about 20%. A more referred concentration is between about 1% and about 6%.

By skin is meant any epidermal tissue in which psoriasis may occur, including that on limbs, trunk, head, as well as mucosa, etc.

As used here, carbamazepine is intended to mean 5-carbamoyl-5H-dibenz[b,f]azepine and pharmaceutically acceptable and stable salts and therapeutically effective derivatives thereof. Without intending to be limited by the mode of action, it is believed that carbamazepine, applied topically, penetrates the skin from the outside to provide a therapeutic effect as when during systemic exposure the carbamazepine enters the skin from the fine capillaries.

In one embodiment of the invention, an oil in water emulsion is prepared to form an elegant cream. Carbamazepine in pure powder form is dissolved in propylene glycol (e.g. up to about 95%). Alternatives for the aqueous phase include an alcohol such as ethanol or isopropanol, with a thickener added, for example Carbomer 934 or 940. The oil phase preferably includes mineral oil, petrolatum, cetyl alcohol, and/or stearyl alcohol. Emulsifiers such as polysorbate 80, sorbitan monostearate, or others known in the art may be used. Buffering agents, antioxidants, and chelating agents may be added to improve the characteristics of the formulation.

In another embodiment, an ointment is prepared by micronizing carbamazepine to provide particles with a size distribution primarily below 10 microns, and adding it to mineral oil to form a finely dispersed suspension, which is then mixed with petrolatum.

EXAMPLE 1

A gel is prepared comprising the following ingredients. Concentrations are given in weight-percent.

| | |
|---|---|
| Carbamazepine | 5% |
| propylene glycol | 93% |
| Carbomer 934 neutralized with sodium hydroxide | 2% |

EXAMPLE 2

A cream is prepared comprising the following ingredients.

| | |
|---|---|
| Carbamazepine | 1% |
| propylene glycol | 50% |
| cetostearyl alcohol | 5% |
| sodium lauryl sulfate | 1% |
| Water | 43% |

EXAMPLE 3

An ointment is prepared with the following ingredients.

| | |
|---|---|
| Carbamazepine | 3% |
| mineral oil | 5% |
| petrolatum | 92% |

EXAMPLE 4

Carbamazepine 5% in propylene glycol and the formulations of the preceding examples are applied daily to the skin of a mouse with experimentally induced model of psoriasis induced by UV light. Based on observation of the size and number of lesions and plaques, the topical carbamazepine treatment is more effective than a placebo for each vehicle lacking the carbamazepine used as a control.

The embodiments illustrated and discussed in this specification are intended only to teach those skilled in the art the best way known to the inventors to make and use the invention. Nothing in this specification should be. considered as limiting the scope of the present invention. Modifications and variations of the above-described embodiments of the invention are possible without departing from the. invention, as appreciated by those skilled in the art in light of the above teachings. It is therefore to be understood that, within the scope of the claims and their equivalents, the invention may be practiced otherwise than as specifically described.

What is claimed is:

1. A method of treating a psoriasis skin condition of a patient comprising applying carbamazepine topically to the patient's stkin repeatedly until the condition improves.

2. A method according to claim 1, wherein the carbamazepine is in a formulation comprising an acceptable non-solid vehicle and carbamazepine, and wherein the vehicle is a cream, ointment, liquid, lotion, or gel.

3. A method according to claim 1, wherein the carbamazepine has a concentration high enough to be effective as applied but not so high as to cause systemic side effects.

4. A method according to claim 2, wherein the carbamazepine has a concentration between about 0.05% and about 20%.

5. A method according to claim 2, wherein the carbamazepine has a concentration between 1% and about 6%.

6. A method of administering carbamazepine comprising applying the carbamazepine topically at a site of a psoriasis skin condition, the carbamazepine having a localized therapeutic effect at the site.

7. A method according to claim 6, wherein the carbamazepine is applied as a therapeutic formulation comprising a topically acceptable non-solid vehicle and carbamazepine, the vehicle consisting of components that are compatible with the carbamazepine, and the carbamazepine being in a concentration sufficient to permit a therapeutically effective amount of the carbamazepine to be absorbed from the formulation into the skin of a patient.

8. A method according to claim 6 comprising applying carbamazepine in a topically acceptable vehicle topically to the patient's skin.

9. A method according to claim 1, wherein the carbamazepine is absorbed into psoriatic skin of a patient in an amount effective to treat the psoriasis.

10. A method according to claim 1, wherein the carbamazepine is in pure form or is a pharmaceutically acceptable stable salt or derivative thereof.

11. A method according to claim 2, wherein the vehicle comprises a component selected from the group consisting of alcohol, acetone, propylene glycol, and combinations.

12. A method according to claim 11, wherein the vehicle comprises propylene glycol.

13. A method according to claim 11, wherein the alcohol comprises ethanol and/or isopropanol.

14. A method according to claim 2, wherein the formulation comprises from about 0.05% to about 20% carbamazepine and up to about 95% propylene glycol.

15. A method according to claim 1, wherein the formulation further comprises a thickener.

16. A method according to claim 15, wherein the thickener comprises Carbomer 934 and/or Carbomer 940.

17. A method according to claim 2, wherein the formulation is an emulsion comprising an oil and water.

18. A method according to claim 17, wherein the oil is selected from the group consisting of mineral oil, petrolaturn, cetyl alcohol, and stearyl alcohol.

19. A method according to claim 2, wherein the formulation further comprises an emulsifier.

20. A method according to claim 19, wherein the emulsifier comprises polysorbate 80 and/or sorbitan monostearate.

21. A method according to claim 2, wherein the formulation further comprises a buffer agent, antioxidant and/or chelating agent.

22. A method according to claim 2, wherein the formulation further comprises an anti-inflammatory agent.

23. A method according to claim 22, wherein the anti-inflammatory agent comprises steroid and/or non-steroid compounds.

24. A method according to claim 2, wherein the formulation further comprises an anesthetic agent.

25. A therapeutic formulation comprising a topically acceptable non-solid vehicle and carbarnazpine, the vehicle consisting of components that are compatible with the carbamazepine, and the carbarnazepine being in a concentration sufficient to permit a therapeutically effective amount of the carbamazepine to be absorbed from the formulation into the skin of a patient having a psoriasis skin condition when administered locally at a site of administration, the formulation having a localized therapeutic effect at the site of administration, and wherein the formulation is a gel consisting essentially of about 5% carbarnzepine, about 93% propylene glycol, and about 2% Carbomer 934 neutralized with sodium hydroxide.

26. A therapeutic formulation comprising a topically acceptable non-solid vehicle and carbamazepine, the vehicle consisting of components that are compatible with the carbamazepine, and the carbamazepine being in a concentration sufficient to permit a therapeutically effective amount of the carbamazepine to be absorbed from the formulation into the skin of a patient having a psoriasis skin condition when administered locally at a site of administration, the formulation having a localized therapeutic effect at the site of administration, and wherein the formulation is a cream consisting essentially of about 1% carbamazepine, about 50% propylene glycol, about 5% cetostearyl alcohol, about 1% sodium lauryl sulfate and about 43% water.

27. A therapeutic formulation comprising a topically acceptable non-solid vehicle and carbarnazepine, the vehicle consisting of components that are compatible with the carbamazepine, and the carbamazepine being in a concentration sufficient to permit a therapeutically effective amount of the carbamazepine to be absorbed from the formulation into the skin of a patient having a psoriasis skin condition when administered locally at a site of administration, the formulation having a localized therapeutic effect at the site of administration, and wherein the formulation is an ointment consisting essentially of about 3% carbamazepine, about 5% mineral oil, and about 92% petrolatum.

* * * * *

UNITED STATES PATENT AND TRADEMARK OFFICE
CERTIFICATE OF CORRECTION

PATENT NO.     : 6,486,152 B1                                       Page 1 of 1
DATED          : November 26, 2002
INVENTOR(S)    : Marc Coles and Gad Keren It is certified that error appears in the above-identified patent and that said Letters Patent is hereby corrected as shown below:

<u>Title page,</u>
Item [75], should read as follows:
-- Inventor:  Gad Keren, Kiriat, Ono (IL) --

Signed and Sealed this

Fifteenth Day of April, 2003

JAMES E. ROGAN
*Director of the United States Patent and Trademark Office*